United States Patent [19]

Bogdanovic et al.

[11] Patent Number: 4,832,934

[45] Date of Patent: May 23, 1989

[54] PROCESS FOR PREPARING HALOGEN MAGNESIUM ALANATE AND USE THEREOF

[75] Inventors: Borislav Bogdanovic; Manfred Schwickardi, both of Mülheim/Ruhr, Fed. Rep. of Germany

[73] Assignee: Studiengesellschaft Kohle mbH, Mulheim, Fed. Rep. of Germany

[21] Appl. No.: 129,803

[22] Filed: Dec. 7, 1987

Related U.S. Application Data

[63] Continuation-in-part of Ser. No. 918,161, Oct. 10, 1986, abandoned.

[30] Foreign Application Priority Data

Oct. 16, 1985 [DE] Fed. Rep. of Germany ....... 3536797

[51] Int. Cl.$^4$ ............................ C01B 6/24; C01B 9/00
[52] U.S. Cl. .................................. 423/463; 423/495; 423/497; 423/644
[58] Field of Search ............... 423/495, 497, 472, 463, 423/465, 644, 647

[56] References Cited

U.S. PATENT DOCUMENTS

| | | | |
|---|---|---|---|
| 2,567,972 | 9/1951 | Schlesinger et al. | 423/644 |
| 2,920,935 | 1/1960 | Finholt | 423/644 |
| 2,994,587 | 8/1961 | Vose | 423/647 |
| 3,030,184 | 4/1962 | Faust et al. | 423/647 |
| 3,179,490 | 4/1965 | Musinski et al. | 423/644 |
| 3,180,700 | 4/1965 | Robinson | 423/644 |
| 3,207,570 | 9/1965 | Noth | 423/644 |
| 3,210,150 | 10/1965 | Powers | 423/644 |
| 3,337,308 | 8/1967 | Verdieck et al. | 423/644 |
| 3,366,453 | 1/1968 | Kloefer et al. | 423/647 |
| 3,387,948 | 6/1968 | Synder | 423/644 |
| 3,666,416 | 5/1972 | Henle et al. | 423/644 |
| 3,849,542 | 11/1974 | Snover et al. | 423/644 |
| 3,926,833 | 12/1975 | Hoffman et al. | 423/495 |
| 4,493,784 | 1/1985 | Mamantov et al. | 423/495 |
| 4,554,152 | 11/1985 | Bogdanovic | 423/647 |
| 4,554,153 | 11/1985 | Bogdanovic | 423/647 |

FOREIGN PATENT DOCUMENTS

| | | | |
|---|---|---|---|
| 0157297 | 10/1985 | European Pat. Off. | 423/647 |
| 2804445 | 8/1979 | Fed. Rep. of Germany | 423/647 |
| 0777095 | 6/1957 | United Kingdom | 423/647 |

OTHER PUBLICATIONS

Chem. Abstract 67:118688s (1967), vol. 67.
Chem. Abstract: 90:161359x, vol. 90 (1979).
Inorganic Chem., vol. 2, No. 3 (Jun. 1963), "Direct Synthesis of Complex Metal Hydrides", Ashby et al., (pp. 499+).
J. Appl. Chem., vol. 10, Apr. 1960, "Prep of Magnesium Hydride", Faust et al., (pp. 187+).
Chem. Abstract, vol. 107, 77308s, Apr. 1987.

*Primary Examiner*—Anthony McFarlane
*Attorney, Agent, or Firm*—Sprung Horn Kramer & Woods

[57] ABSTRACT

The present invention relates to $[Mg_2X_3 (Ether)_y]^+ [AlH_4]^-$ in which
X is halogen,
ether is an aliphatic or cyclic ether, and
y is from 0 to 6.

17 Claims, No Drawings

PROCESS FOR PREPARING HALOGEN MAGNESIUM ALANATE AND USE THEREOF

This is a continuation-in-part of Application Ser. No. 918,161, filed Oct. 10, 1986, now abondoned.

The invention relates to a process for an easy preparation of halogen magesium alanate XMgAlH$_4$ (X=Cl, Br, I) and the use thereof.

Reductions using complex metal hydrides are standard reactions in organic chemistry (cf., e.g., N. G. Gaylord, "Reduction with Complex Metal Hydrides", Interscience Publishers, Inc., New York 1956). In these reactions the ether-soluble LiAlH$_4$ is most frequently used. In principle the substitution of the expensive lithium by the less expensive magnesium should result in a cost reduction.

Therefore, many attempts have been made at synthesizing Mg(AlH$_4$)$_2$. Contradictory statements are found in the literature with respect to the properties of said substance. An ether-soluble Mg(AlH$_4$)$_2$ was first described by Wiberg and Bauer (Z. Naturfosch. 5B, 397 (1950); Z. Naturforsch. 7b, 131 (1952), German Pat. No. 845 338):

$$2\ LiAlH_4 + MgBr_2 \rightarrow Mg(AlH_4)_2 + 2\ LiBr$$
$$4\ MgH_2 + AlCl_3 \rightarrow Mg(AlH_4)_2 + 3\ MgCl_2$$
$$MgH_2 + AlH_3 \rightarrow Mg(AlH_4)_2$$

The MgH$_2$ to be employed in these reactions was obtained by the thermolysis of Grignard or diorganomagnesium compounds, respectively. In this reaction in addition to magnesium halide also alkenes are formed as undesired by-products. However, a synthesis starting from the lithium alanate is inappropriate. According to A. Hertwig {German Pat. No. 921 986 (1954); C.A. 52, 11371 d)} the reaction of Grignard compounds with Al halides and hydrogen results in the formation of chloromagnesium alanate, ClMgAlH$_4$, which may be converted into magnesium alanate by thermolysis.

$$4\ RMgX + AlX_3 + 4H_2 \rightarrow XMg(AlH_4) + 3\ MgX_2 + 4\ RH$$

$$2\ XMg(AlH_4) \rightarrow Mg(AlH_4)_2 + MgX_2$$

The reaction of a mixture of MgH$_2$ and aluminum with aluminum chloride gives Mg(AlH$_4$)$_2$(BP 785 348). The reaction of MgH$_2$ with aluminum and hydrogen under drastic reaction conditions {J. C. Snyder, U.S. Pat. No. 3,387,948 (1962) } provides Mg(AlH$_4$)$_2$ in insatisfactory yields. All of the described processes do not satisfy the requirements for commercial procedures.

The Mg(AlH$_4$)$_2$ synthesized later {J. Plesek, S. Hermanek, Coll. Czech. Chem. Comm. 31, 3060 (1966) } from magnesium halide and sodium alanate, in contrast to earlier descriptions, had an extremely poor solubility in ethers. According to Ashby et al. {(Inorg. Chem. 9, 325 (1970)} in the reactions of lithium alanate with magnesium bromide or magnesium hydride with aluminum chloride a soluble halogenomagnesium alanate, XMg(AlH$_4$), is formed as a product which is also obtainable from hydride magnesium chloride and alane {(Inorg. Chem. 16, 2941 (1977)}. Thus, the true constitution of the reaction product has not been recognized by Wiberg, Hertwig and Snyder.

The substitution of the expensive lithium alanate with the less expensive soluble halogen magnesium alanate still appears to be desirable. The realization of this concept has so far failed due to the lack of an efficient synthesis for the inexpensive starting material magnesium hydride.

According to the European Pat. No. 0 003 564 metallic magnesium may be hydrogenated by means of homogeneous transition metal catalysts under mild conditions to give magnesium hydride which, contrary to the magnesium hydride produced in accordance with conventional processes (high temperature hydrogenation) has a high reactivity. This method for preparing hydrides of magnesium by using hydrogen and transition metal catalysts is characterized in that magnesium is reacted with hydrogen in the presence of a catalyst consisting of a halide of a metal of the Subgroups IV to VIII of the Periodic Table and an organomagnesium compound or a magnesium hydride, and optionally in the presence of a polycyclic aromatic or a tertiary amine and optionally in the presence of magnesium halide MgX$_2$ wherein X=Cl, Br, I.

In the subclaims of the European Patent Specification No. 0 003 564 preferred embodiments have been claimed, namely that the reaction is carried out in a solvent, preferably in tetrahydrofurane, that pressures of from 1 to 300 bar and temperatures of from 0° C. to 200° C. are employed, that the ratio of Mg: transition metal is selected to be from 10$^4$ to 10:1, and the ratio of transition metal: organomagnesium compound or magnesium hydride is selected to be from 0.1:1 to 10:1, chromium, titanium and iron halides are employed as the transition metal halides, magnesium anthracene is used as the organomagnesium compound, anthracene, tetracene and benzanthracene are employed as the polycyclic aromatics, and tertiary amines NR$_3$ are used wherein R=alkyl or cycloalkyl groups and that optionally, when the magnesium is allowed to react, its halides MgX$_2$ wherein X=Cl, Br, I, are added in the ratio of Mg: MgX$_2$=1:1.

It has now been found that the highly active magnesium hydride which is now readily available due to said process is excellently suitable for the production of halogen magnesium alanates from aluminum halides.

Accordingly, the present invention relates to a process for preparing halogen magnesium alanates of the formula $$[Mg_2X_3(Ether)y]^+[AlH_4]^-$$

wherein
X is halogen,
Ether is an aliphatic or cyclic ether, and
Y is from 0 to 6
from aluminum halide and magnesium hydride, which process is characterized in that an aluminum halide AlX$_3$ is reacted with a magnesium hydride in an ether solvent, said magnesium hydride having been prepared from magnesium and hydrgen in a solvent in the presence of homogeneous catalysts consisting of a halide of a metal of the Subgroups IV to VIII of the Periodic System and of an organomagnesium compound or a magnesium hydride and in the presence of a polycyclic aromatic or of a tertiary amine and optionally in the presence of a magnesium halide MgX$_2$, e.g. X=Cl, Br, I.

The reaction proceeds in aprotic organic solvents, and preferably cyclic or linear ethers or polyethers such as tetrahydofurane (THF) or Glyme (monoglyme or diglyme), already at below 0° C. and gives halogen magnesium alanates in high yields. THF is particularly preferred.

The reaction of the aluminum halide with the magnesium hydride is preferably carried out in the temperature range of from −80° C. to 150° C., the range of from −10° C. to 60° C. being particularly preferred.

The combination of the two processes enables a two-step synthesis of halogen magnesium alanates to be effected using the inexpensive raw materials magnesium, hydrogen and aluminum halide as exemplified hereinbelow:

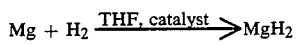

Catalyst:
1 mole percent of anthracene,
1 mole percent of CrCl$_3$ or TiCl$_4$

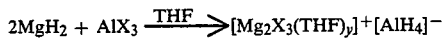

X=Cl, Br, I

Alternatively, there is the possibility of isolating the MgH$_2$ prepared according to the European Pat. No. 0 003 564 in the solid state and then to use the compound in a different suitable solvent for the reaction with aluminum halides.

According to own investigations, the product cannot be successfully prepared by using commercially available MgH$_2$ synthesized from the elements at high temperatures. Even upon activation by grinding in a glass ball mill such a magnesium hydride does not yield reduction products in the reaction with unsaturated substrates, as will be apparent from the Comparative Example.

The chloromagnesium alanate prepared according to the present invention may be employed for reduction purposes directly as a solution or, upon removal of the solvent, as a solid. The MgCl$_2$ formed as a by-product does not interfere with the subsequent reactions; in the case of the isolated material the pyrophoricity of the materials is even lowered. If, however, it is desired to remove the produced MgCl$_2$, this is possible by the addition of dioxane.

The product as readily available from MgH$_2$ and AlCl$_3$ is a very good reducing agent for functional organic groups. It has been shown (cf. EXAMPLES) that aldehydes, esters, ketones, alkyl halides, carboxylic acids and anhydrides are reduced in very good yields. A change of the solvents for the reductions is possible.

The obtained yields are often better than those attained by Wiberg and Bauer {Chem. Ber. 85, 593(1952)}. The reduction power of the product is comparable to that of LiAlH$_4$, and replacing the expensive lithium with the inexpensive magnesium is feasible and desirable. A further advantage of this method is that the hydrogenation of magnesium and subsequent reduction of functional organic compounds may be carried out in a single-vessel reaction, e.g. in THF as reaction medium.

The invention is illustrated in greater detail by the following EXAMPLES. All experiments were run in absolute solvents under argon as protective gas.

EXAMPLE 1

48 ml of a 4.12 molar MgH$_2$ suspension (prepared according to the European Pat. No. 0 003 564 with a chromium catalyst; Mg: anthracene: CrCl$_3$=100: 1:1) were charged into 250 ml three-necked flask equipped with dropping funnel, reflux condenser and inner thermometer. To this well agitated suspension there were dropwise added 8.85 g (66 mmol) of AlCl$_3$, dissolved in 60 ml of THF within a period of 30 min so that the inside temperature did not exceed 30° C. (external cooling), resulting in formation of the [AlH$_4$]$^-$. Then 25.3 ml (239 mmol) of 3-pentanone were immediately added dropwise within 20 min. (exothermal reaction, external cooling). The mixture was allowed to after-react at room temperature for 1 h; then the volatile reaction products were removed under the vacuum of an oil pump. The residue was suspended in 60 ml of toluene and decomposed with H$_2$O and HCl. The organic phase was separated, and the aqueous phase was twice extracted with toluene. The united organic phases were distilled at from 20° C. to 120° C./0.1 mbar.

An aliquot was admixed with n-octane and subjected to gas chromatographic analysis. Yield: 19.98 g of 3-pentanol (95% of the theoretical value).

EXAMPLE 2

The experiment was carried out as in EXAMPLE 1, but using 60 ml of a 3.42 molar MgH$_2$ suspension, 6,63 g of AlCl$_3$(50 mmol) in 59 ml of THF and 17.2 ml (169 mmol) of benzaldehyde.

Yield: 16.96 g (157 mmol) of benzyl alcohol (93% of the theoretical value).

EXAMPLE 3

The experiment was carried out as in EXAMPLE 1, but using 50 ml of a 4.12 molar MgH$_2$ suspension, 8.02 g of AlCl$_3$ (60 mmol) in 60 ml of THF and 15.5 ml (108 mmol) of benzoic acid ethyl ester.

Yield: 11.67 g (108 mmol) of benzyl alcohol (100% of the theoretical value).

EXAMPLE 4

The experiment was carried out as in EXAMPLE 1, but using 70 ml of a 2.94 molar MgH$_2$ suspension, 8.5 g of AlCl$_3$(64 mmol) in 60 ml of THF and 34 ml (216 mmol) of 1-bromoheptane.

Yield: 19.34 g (193 mmol) of n-heptane (89% of theoretical value).

EXAMPLE 5

The experiment was carried out as in EXAMPLE 1, but using 30 ml of a 6.33 molar MgH$_2$ suspension, 4.08 g of AlCl$_3$ (30.6 mmol) in 48 ml of THF and 8.5 ml (104 mmol) of crotonaldehyde.

Yield: 6.79 g (94.2 mmol) of crotyl alcohol (91% of the theoretical value).

EXAMPLE 6

The experiment was carried out as in EXAMPLE 1, but using 70 ml of a 3.01 molar MgH$_2$ suspension, 9.28 g of AlCl$_3$ (70 mmol) in 74 ml of THF and 9.4 ml (59.3 mmol) of octanoic acid.

Yield: 7.15 g (54.9 mmol) of 1-octanol (93% of theoretical value).

EXAMPLE 7

The experiment was carried out as in EXAMPLE 1, but using 42 ml of a 5.88 molar MgH$_2$ suspension, 11.0 g of AlCl$_3$ (82.6 mmol) in 100 ml of THF and 6.0 ml (46.8 mmol) of propionic acid anhydride.

Yield: 5.371 g (89.4 mmol) of 1-propanol (95% of the theoretical value).

EXAMPLE 8

The experiment was carried out as in EXAMPLE 1, but using 40 ml of a 2.7 molar $MgH_2$ suspension, 4.77 g of $AlCl_3$ (36 mmol) in 44 ml of THF and 10.4 ml (102 mmol) of benzaldehyde at 65° C.

Yield: 8.87 g (82.0 mmol) of benzyl alcohol (80% of the theoretical value).

EXAMPLE 9

The experiment was carried out as in EXAMPLE 1, but using 2.40 g (91.1 mmol) of isolated and dried $MgH_2$, 3.92 g of $AlCl_3$ (29.4 mmol) in 66 ml of THF and 10.1 ml (100 mmol) of benzaldehyde.

Yield: 8.61 g (79.6 mmol) of benzyl alcohol (80% of the theoretical value).

EXAMPLE 10

The experiment was carried out as in EXAMPLE 1, but using 2.40 g (91.1 mmol) of isolated and dried $MgH_2$ prepared using a titanium catalyst, 3.92 g of $AlCl_3$ (29.4 mmol) in 66 ml of THF and 10.1 ml (100 mmol) of benzaldehyde.

Yield: 8.61 g (79.6 mmol) of benzyl alcohol (80% of the theoretical value).

COMPARATIVE EXAMPLE

The experiment was carried out using 6.11 g (197 mmol) of 85% commercially available $MgH_2$ which and been activated by grinding in a glass ball mill for 2 h, 6.74 g of $AlCl_3$ (50.5 mmol) in 60 ml of THF and 13.0 ml (90.5 mmol) of benzoic acid ethyl ester in the same manner as in EXAMPLE 1. Besides the starting compound no benzyl alcohol was detectable by gas chromatography.

It will be understood that the specification and examples are illustrative but not limitative of the present invention and that other embodiments within the spirit and scope of the invention will suggest themselves to those skilled in the art.

We claim:

1. A compound according to the formula $[Mg_2X_3(Ether)y]^+[AlH_4]^-$
in which
X is halogen,
Ether is an aliphatic or cyclic ether, and
y is from 0 to 6.

2. A compound according to claim 1, in which X is chlorine.

3. A compound according to claim 1, in which y is 6.

4. A compound according to claim 1, in which Ether is a cyclic or linear ether or polyether.

5. A compound according to claim 1, in which Ether is tetrahydrofurane, monoglyme or diglyme.

6. A compound according to claim 1, wherein the formula is $[Mg_2Cl_3(THF)_6]^+[AlH_4]^-$.

7. A process for preparing a compound of the formula $[Mg_2X_3(Ether)y]^+[AlH_4]^-$ in which
X is halogen,
ether is an aliphatic or cyclic ether, and
y is from 0 to 6, comprising reacting an aluminum halide with a magnesium hydride in a solvent, said magnesium hydride having been prepared from magnesium and hydrogen in a solvent in the presence of a homogeneous catalyst consisting essentially of a halide of a metal of the Subgroups IV to VIII of the Periodic System and of (a) an organomagnesium compound or (b) a magnesium hydride, and in the presence of a polycyclic aromatic or of a tertiary amine.

8. The process according to claim 7, wherein the magnesium hydride is prepared in the presence of a magnesium halide in addition to the polycyclic aromatic or tertiary amine.

9. The process according to claim 7, wherein the solvent is an aprotic organic solvent.

10. The process according to claim 9, wherein the solvent is an aliphatic or alicyclic ether.

11. The process according to claim 10, wherein the solvent is tetrahydrofurane, monoglyme or diglyme.

12. The process according to claim 9, wherein the reaction of the aluminum halide with the magnesium hydride is carried out in the temperature range of from $-80°$ C. to 150° C.

13. The process according to claim 9, wherein the reaction of the aluminum halide with the magnesium hydride is carried out in the temperature range of from $-10°$ C. to 60° C.

14. The process according to claim 9 carried out in two steps, the magnesium hydride being prepared in the first step and then the magnesium hydride being reacted with the aluminum halide in the second step in the same solvent.

15. The process according to claim 14, wherein the solvent is tetrahydrofurane and the reaction of the aluminum halide with the magnesium hydride is carried out in the temperature range of from $-10°$ C.

16. The process according to claim 10, wherein y is 6.

17. The process according to claim 11, wherein y is 6.

* * * * *

UNITED STATES PATENT AND TRADEMARK OFFICE
CERTIFICATE OF CORRECTION

PATENT NO. : 4,832,934

DATED : May 23, 1989

INVENTOR(S) : Bogdanovic et al.

It is certified that error appears in the above-identified patent and that said Letters Patent is hereby corrected as shown below:

Col. 4, line 6          After "the" add -- compound $[Mg_2Cl_3(THF)_6]^+$ --

Col. 6, line 47        After "-10°C." add --to 60°C.--

Signed and Sealed this

Twentieth Day of November, 1990

Attest:

HARRY F. MANBECK, JR.

*Attesting Officer*        *Commissioner of Patents and Trademarks*